(12) United States Patent
Gallo, Sr.

(10) Patent No.: US 8,444,601 B2
(45) Date of Patent: May 21, 2013

(54) SUCTION FLOW REGULATOR

(75) Inventor: David P. Gallo, Sr., Naples, FL (US)

(73) Assignee: Arthrex, Inc., Naples, FL (US)

( * ) Notice: Subject to any disclaimer, the term of this patent is extended or adjusted under 35 U.S.C. 154(b) by 646 days.

(21) Appl. No.: 12/639,336

(22) Filed: Dec. 16, 2009

(65) Prior Publication Data
US 2010/0160909 A1 Jun. 24, 2010

Related U.S. Application Data

(60) Provisional application No. 61/138,034, filed on Dec. 16, 2008.

(51) Int. Cl.
*A61M 1/00* (2006.01)
*A61B 18/14* (2006.01)

(52) U.S. Cl.
USPC ............................................. 604/118; 606/41

(58) Field of Classification Search
USPC ................. 606/41, 1; 604/118–119, 317–357
See application file for complete search history.

(56) References Cited

U.S. PATENT DOCUMENTS

| 5,451,222 | A | * | 9/1995 | De Maagd et al. ............. 606/41 |
| 6,592,543 | B1 | | 7/2003 | Wortrich et al. |
| 2001/0044600 | A1 | | 11/2001 | Elkins |
| 2004/0193150 | A1 | | 9/2004 | Sharkey et al. |

FOREIGN PATENT DOCUMENTS
WO  WO 01/35845 A1  5/2001

* cited by examiner

*Primary Examiner* — Michael Peffley
*Assistant Examiner* — Samantha Good
(74) *Attorney, Agent, or Firm* — Dickstein Shapiro LLP (57) ABSTRACT

A suction flow regulator including an adapter and a grommet fixed inside the adapter for permitting air to access a vacuum flow path according to a vacuum level. The grommet is fixed inside an adapter by a securing mechanism (for example, a compression plate). The grommet may be used with an additional elastomeric element (for example, a smaller grommet) that provides flexibility during vacuum exposure and deflects to expose holes in the grommet under vacuum. Alternatively, the grommet may be a single unit grommet with a cantilever configuration.

14 Claims, 8 Drawing Sheets

Section Y-Y

Section Z-Z

SUCTION FLOW REGULATOR

This application claims the benefit of U.S. Provisional Patent Application No. 61/138,034, filed Dec. 16, 2008 and entitled "SUCTION FLOW REGULATOR," which is incorporated herein by reference in its entirety.

FIELD OF THE INVENTION

The present invention relates to the field of surgery and, more particularly, to a system for controlling suction flow of devices used for medical procedures, including ablating devices such as RF ablators.

BACKGROUND OF THE INVENTION

Vacuum systems operating at varying vacuum rates are commonly employed during arthroscopic and other medical procedures. For example, ablating devices—which vaporize tissue via an electrode—either include or are used with a corresponding aspirating device. A direct correlation exists between the ablation efficiency and the level of vacuum experienced at the distal end of the aspirating device. Too little aspiration can pull in pieces of tissue that are too large for the aspirating device, therefore clogging the device. In contrast, too much aspiration sweeps working bubbles, used to transmit current from the electrode to tissue, off the electrode surface before they can be used to arc through. Such an effect is undesirable, because unnecessary working bubble removal requires an increase in the power output of an electrosurgical unit (ESU) to generate bubbles fast enough to allow the arcing before the working bubbles are aspirated away. Increasing the ESU power output when exposing the devices to a high vacuum is not recommended, as currently known ablators require the lowest possible power setting for use.

Current methods of titrating suction in vacuum systems provide insufficient results. Surgeons customarily use clamps—such as a roller clamp, ratcheted tube clamp or even external clamping devices—to titrate suction in vacuum systems. Clamps allow for full on/full off conditions, but are not effective for any controllable titration at other locations. Holes in the suction tubes are more reliable, but require the user (i.e., the surgeon) to determine where a sliding cover would need to be placed over the system and, thus, require additional input from the user. Accordingly, more transparent, automatic and user-friendly systems are needed.

BRIEF SUMMARY OF THE INVENTION

The present invention provides a new suction flow regulator that automatically regulates the vacuum pressure of a medical device to ensure a desired vacuum level at a distal end of the medical device. The suction flow regulator of the present invention allows automatic compensation, so that vacuum requirements of the suction system are met while a more optimal suction effect is delivered at the distal end of a medical device. For example, the suction flow regulator maintains a more regular volumetric flow rate in an aspiration device used during an ablation procedure.

The suction flow regulator comprises a grommet designed to be fixed inside an adapter by a securing mechanism (for example, a compression plate). In an exemplary embodiment, the grommet may be used with an additional elastomeric element (for example, a smaller grommet) that provides flexibility during vacuum exposure and deflects to expose holes in the grommet under vacuum. In another exemplary embodiment, the grommet may be a single piece grommet with a cantilever configuration.

Other features and advantages of the present invention will become apparent from the following description which refers to the accompanying drawings.

DETAILED DESCRIPTION OF THE INVENTION

The present invention provides a new suction flow regulator that automatically regulates the vacuum pressure of a medical device to ensure a desired vacuum level at a distal end of the medical device. The suction flow regulator of the present invention allows automatic compensation, so that vacuum requirements of the suction system are met while a more optimal suction effect is delivered at the distal end of a medical device. For example, the suction flow regulator maintains a more regular volumetric flow rate in an aspiration device used during an ablation procedure.

Embodiments of the suction flow regulator include a grommet fixed inside an adapter by a securing mechanism (for example, a compression plate). In an exemplary embodiment, the grommet may be used with an additional elastomeric element (for example, a smaller or lower grommet) that provides flexibility during vacuum exposure and deflects to expose holes in the grommet under vacuum. In another exemplary embodiment, the grommet may be a single piece grommet with a cantilever configuration.

The suction flow regulator of the present invention may be incorporated into existing aspirating ablators (for example, RF ablation devices), or may be provided as a stand alone version to enable use with other surgical applications and/or devices (to attach to standard tubing sizes, for example) as may be required. The suction flow regulator is transparent to the user (e.g., a surgeon), may be buried in the aspirating ablator device assembly, and allows for an automatic compensation for vacuum exposure to ensure that a more optimized vacuum exposure is experienced at the distal end of an aspirating device during clinical use.

Referring now to the drawings, where like elements are designated by like reference numerals, FIGS. 1-13 illustrate various structural elements of a suction flow regulator. As shown in FIGS. 1-4, suction flow regulator 100 comprises a grommet 20 which has a specific configuration and which is encased within the body of tubing adapter 10 at the proximal end of a suction tube component. Adapter 10 is configured to connect to suction tubing and permit fluid to flow through a vacuum flow path within adapter 10. Securing mechanism 30 (for example, compression plate 30) allows secure engagement of the grommet 20 within the adapter 10. Securing mechanism 30 also includes holes which permit external air to reach grommet 20, as described further below.

Due to the vacuum pressure applied to the suction flow regulator, the grommet may be at risk of being sucked into the adapter at moderate vacuum pressures. Accordingly, the specific design and configuration of the grommet and accompanying adapter can be selected to maintain the grommet in a secure position within the adapter of the suction flow regulator. FIGS. 5-8 and 11-13 illustrate embodiments of suction flow regulators including other configurations of grommets and corresponding adapters. As discussed below, suction flow regulators 200 (FIG. 8) and 300 (FIG. 13) are similar in design to suction flow regulator 100 (FIG. 3), and may be selected based upon the desired vacuum levels and conditions at the distal end of the ablation device or other vacuum system, as well as the tubing and other components used in the vacuum system, among other factors.

Figure 7:
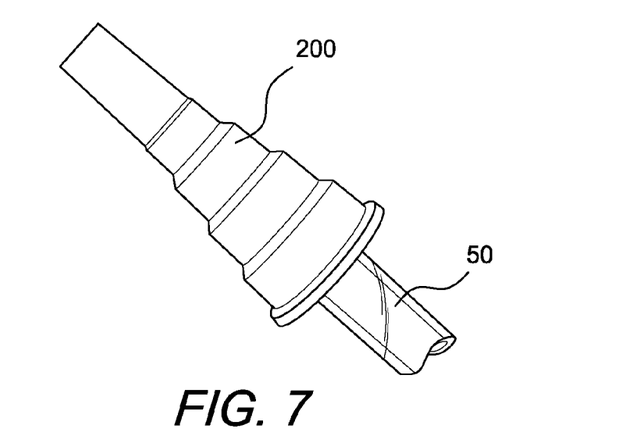
FIG. 7 illustrates the suction flow regulator assembled on a suction tube of an aspirating device.
Figure 8:
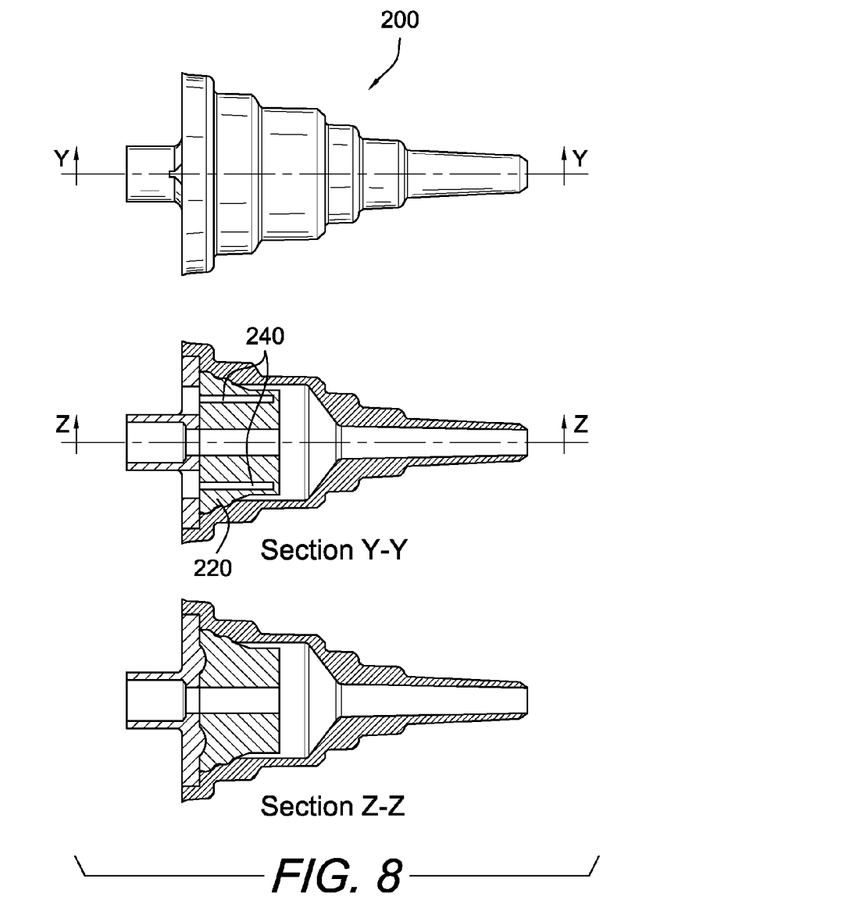
FIG. 8 illustrates various cross-sectional sectional views of the suction flow regulator of FIG. 5.

FIGS. 5-8 illustrate a second embodiment of a suction flow regulator 200 comprising grommet 220 which has a specific configuration and which is encased within the body of tubing adapter 210 at the proximal end of a suction tube component. Securing mechanism 230 (for example, compression plate 230) provided with through holes 235 allows secure engagement of the grommet 220 within the adapter 210. FIG. 7 illustrates suction flow regulator 200 securely engaged to a suction tube component 50 of an aspirating device. Suction flow regulator 200 (as well as suction flow regulators 100 and 300 of FIGS. 1-4 and 11-13, respectively) may, for example, be fixed at a proximal end of a suction tube of an aspirating device, whether within the aspirating device itself or external to the aspirating device.

Figure 11:
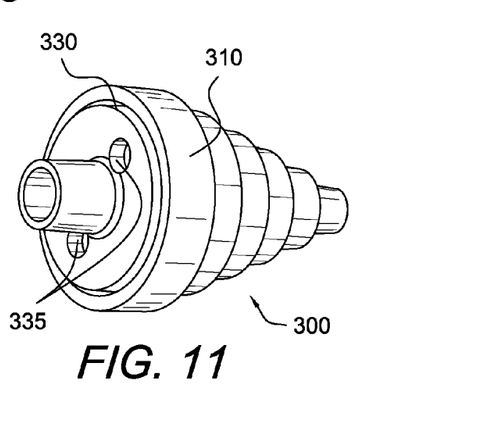
FIG. 11 illustrates a perspective view of a suction flow regulator according to another embodiment.
Figure 12:
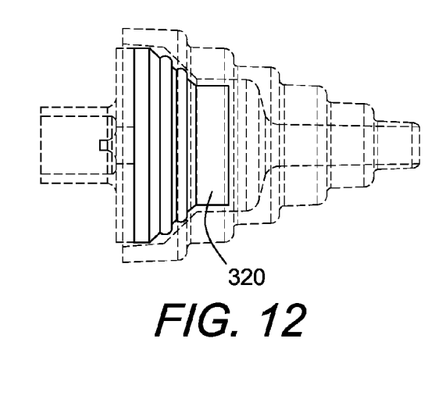
FIG. 12 illustrates a side view of a grommet fixed within the suction flow regulator of FIG. 11.
Figure 13:
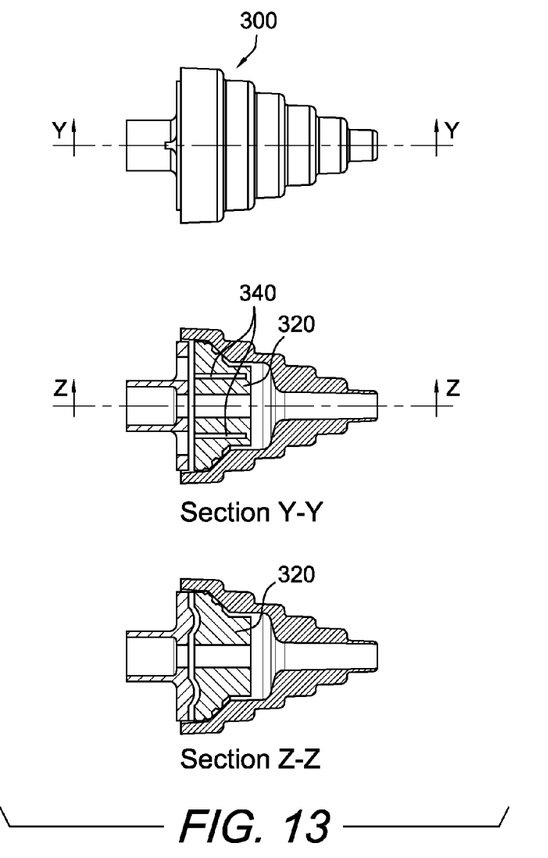
FIG. 13 illustrates various cross-sectional sectional views of the suction flow regulator of FIG. 11.

FIGS. 11-13 illustrate yet another embodiment of a suction flow regulator 300 comprising grommet 320 which has a specific configuration and which is encased within the body of tubing adapter 310 at the proximal end of a suction tube component. Securing mechanism 330 (for example, compression plate 330) provided with through holes 335 allows secure engagement of grommet 320 within adapter 310.

Figure 9:
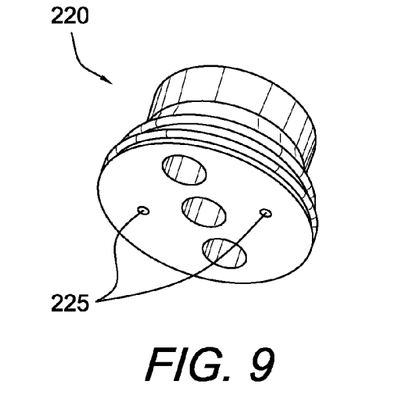
FIG. 9 illustrate a perspective view of a grommet of a suction flow regulator according to a first embodiment.
Figure 10:
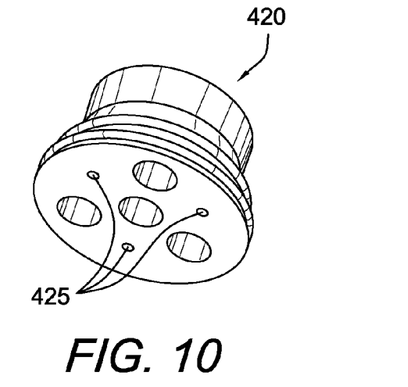
FIG. 10 illustrate a perspective view of a grommet of a suction flow regulator according to a second embodiment.

FIGS. 9 and 10 illustrate various configurations of a grommet in accordance with embodiments described herein. The grommet may include multiple weep holes leading to slits traversing within the grommet. For example, FIG. 9 illustrates grommet 220 having two weep holes 225, and FIG. 10 illustrates grommet 420 having three weep holes 425. As shown in grommet 20 (FIG. 3), grommet 220 (FIG. 8), and grommet 340 (FIG. 13), slits 40, 240, 340, respectively, corresponding to the weep holes in the grommet, allow air flow through the weep holes at high vacuum pressures. The slits and corresponding weep holes may be of the same or different dimensions. For example, the 3 weep hole grommet 420 of FIG. 10 may comprise weep holes 425 with the following diameters: Ø0.021 in; Ø0.026 in; and Ø0.031 in.

Figure 1:
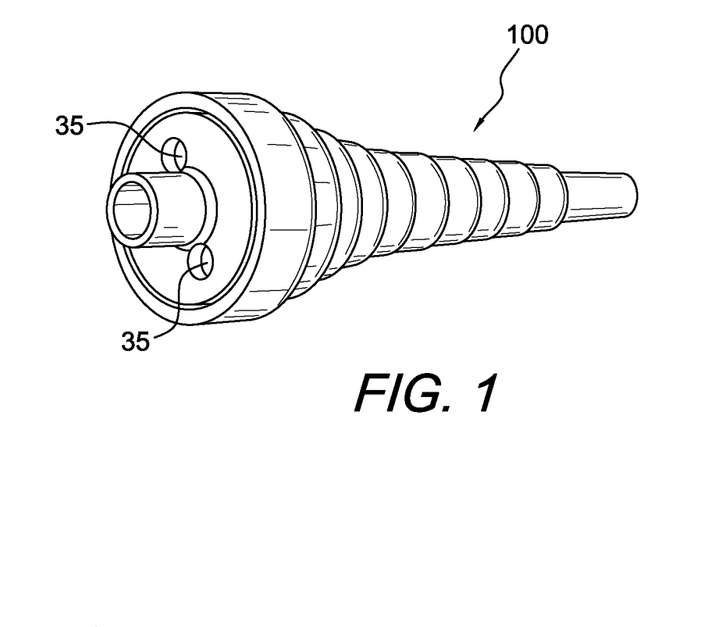
FIG. 1 illustrates a perspective view of a suction flow regulator according to a first embodiment.
Figure 2:
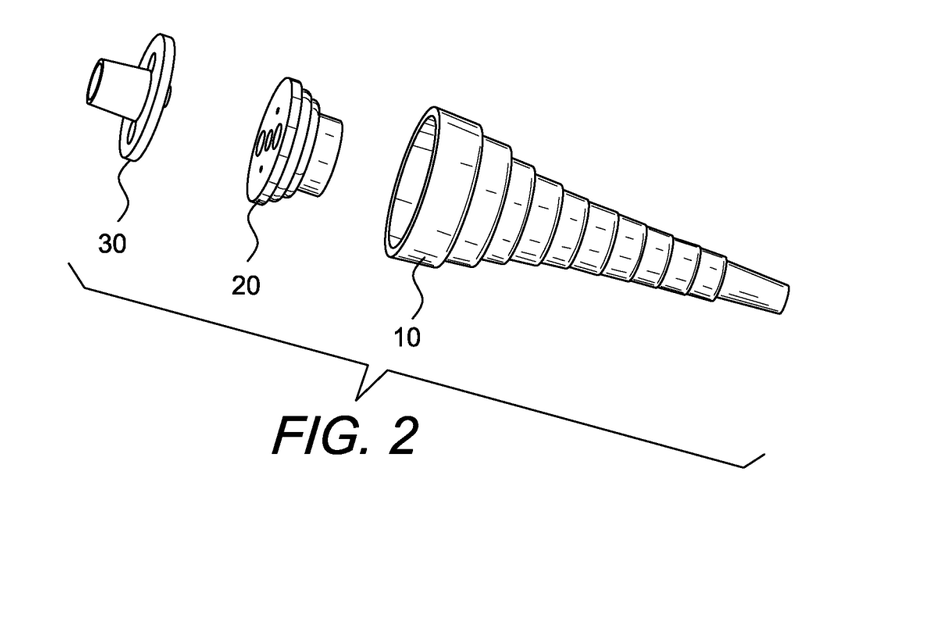
FIG. 2 illustrates an expanded view of the suction flow regulator of FIG. 1.
Figure 3:
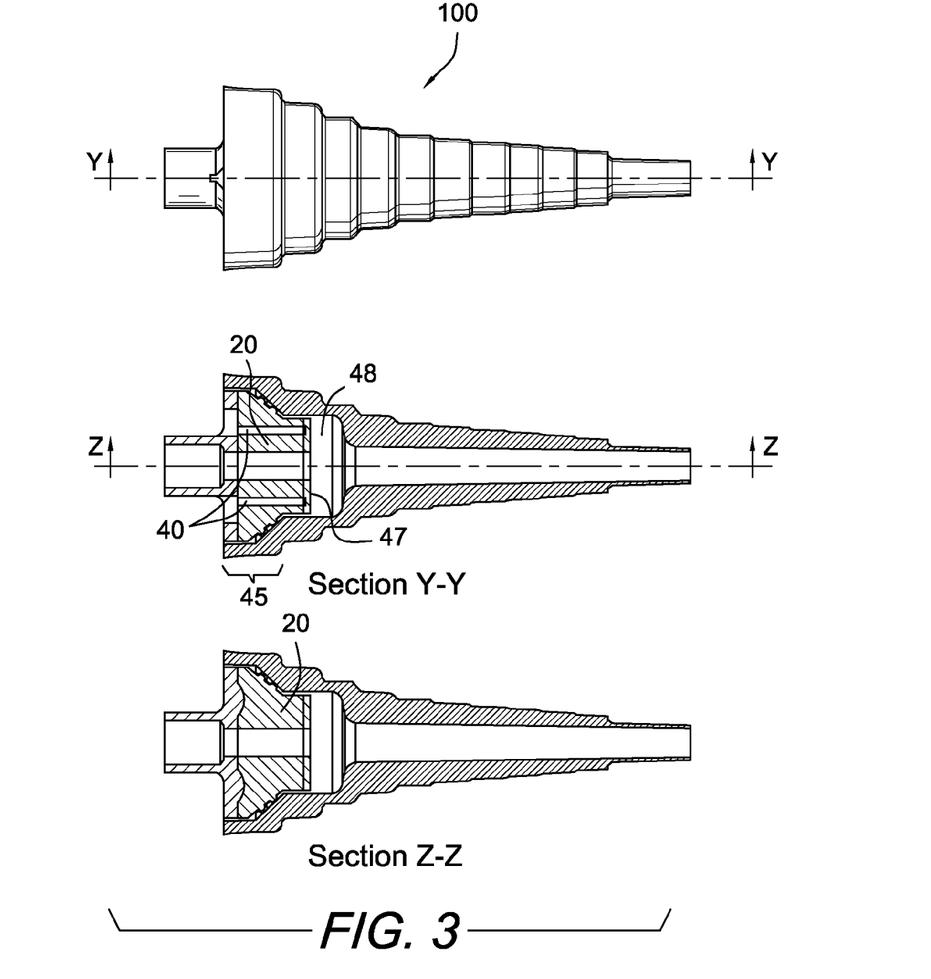
FIG. 3 illustrates various cross-sectional sectional views of the suction flow regulator of FIG. 1.
Figure 4:
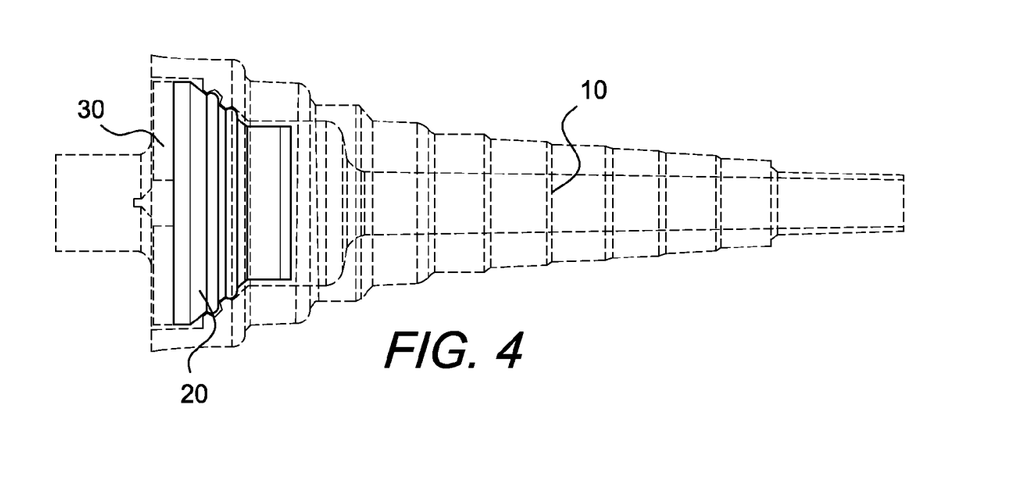
FIG. 4 illustrates a side view of a grommet fixed within the suction flow regulator of FIG. 1.
Figure 5:
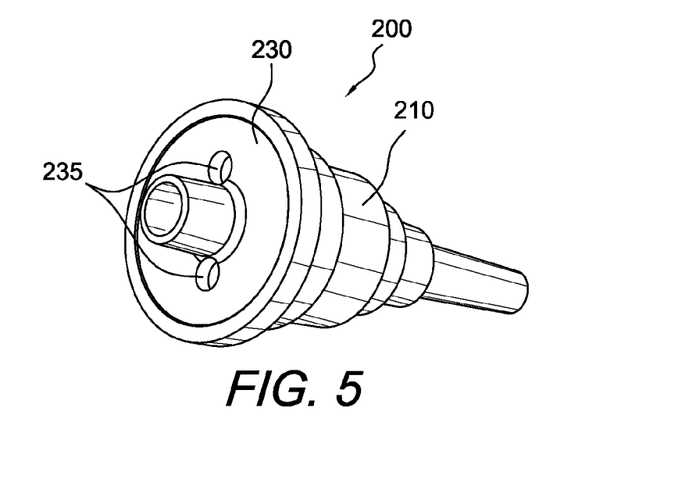
FIG. 5 illustrates a perspective view of a suction flow regulator according to another embodiment.
Figure 6:
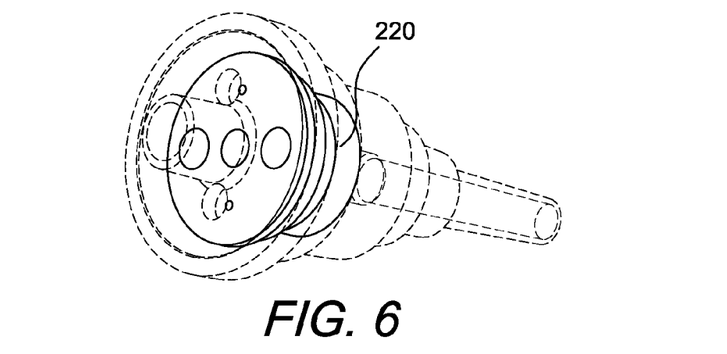
FIG. 6 illustrates a perspective view of a grommet fixed within the suction flow regulator of FIG. 5.

According to an exemplary embodiment only, grommet 20 of the present invention comprises two separate and uniquely-shaped grommet components, as shown in FIG. 3:

a. Main Grommet 45: Higher durometer elastomeric material, intended to be rigid to maintain structural integrity of both the grommet body and integral slits 40 during assembly, compression and clinical use.

b. Lower Grommet 47: Lower durometer elastomeric material, intended to provide the flexibility during vacuum exposure, to act as a curved end cantilever beam under vacuum and to flex to expose openings of slits 40 on the distal end of main grommet 45, thereby forming a fluid path from weep holes 225 (FIG. 9) on a proximal end of main grommet 45 through slits 40 to the distal end of main grommet 45.

At low vacuum levels, the forces exerted across the face of lower grommet 47 are not sufficient to cause it to flex and, therefore, lower grommet 47 will not expose openings of slits 40 on the distal end of main grommet 45 to direct vacuum.

At medium to high vacuum levels, the vacuum creates enough force across the face of lower grommet 47 to induce a deflection, exposing the openings of slits 40 on the distal end of main grommet 45 to a mixing chamber 48 within the body of adapter 10.

Once exposed, air is drawn in from the outside surgical environment, for example through holes 35 in compression plate 30, to the weep holes 225 (FIG. 9) and slits 40 in main grommet 45 into the mixing chamber 48 within the body of adapter 10. The total effect allows the desired vacuum requirements of the suction system to be met, while maintaining a lower, more desirable vacuum level at the distal end of the vacuum device.

Figure 14:
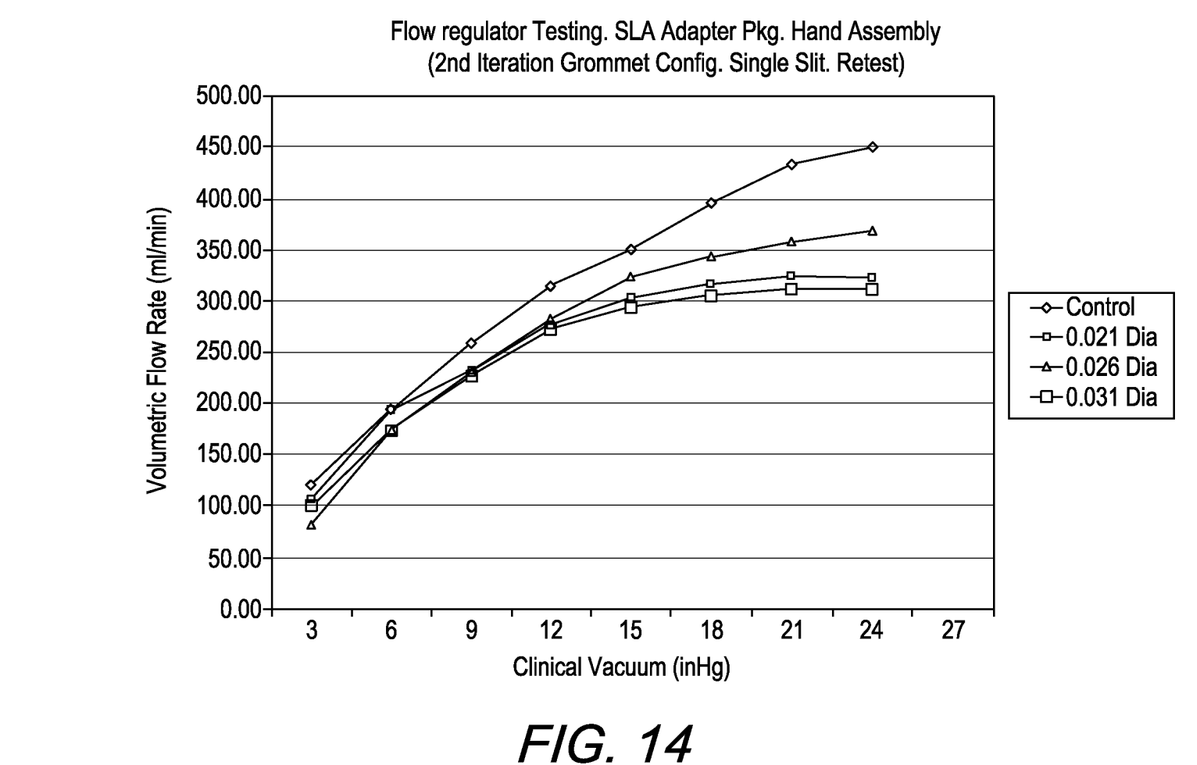
FIGS. 14-16 illustrate various graphs depicting the relationship between the volumetric flow rate and clinical vacuum pressure with different grommets of the suction flow regulator of the present invention.
Figure 15:
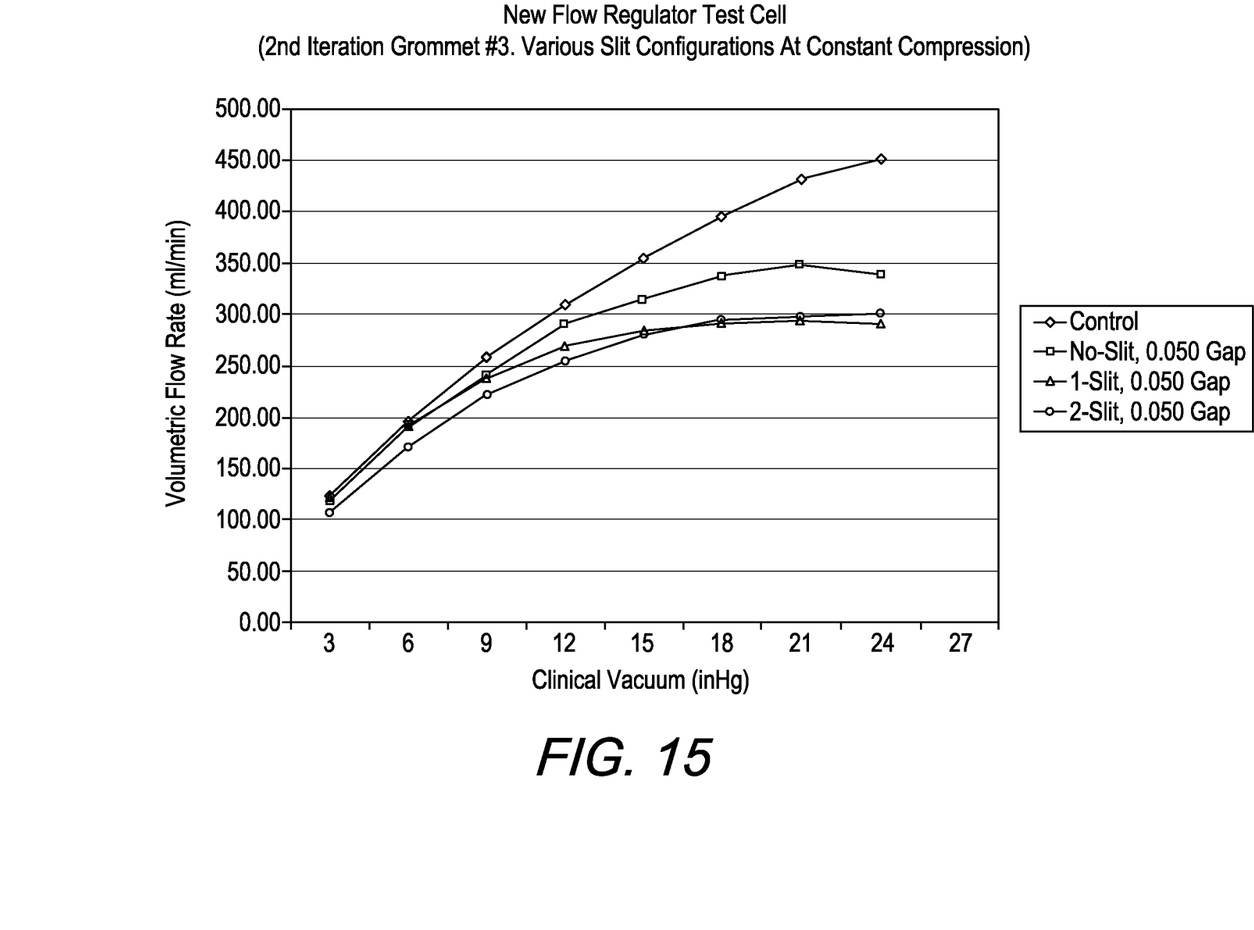
Figure 16:
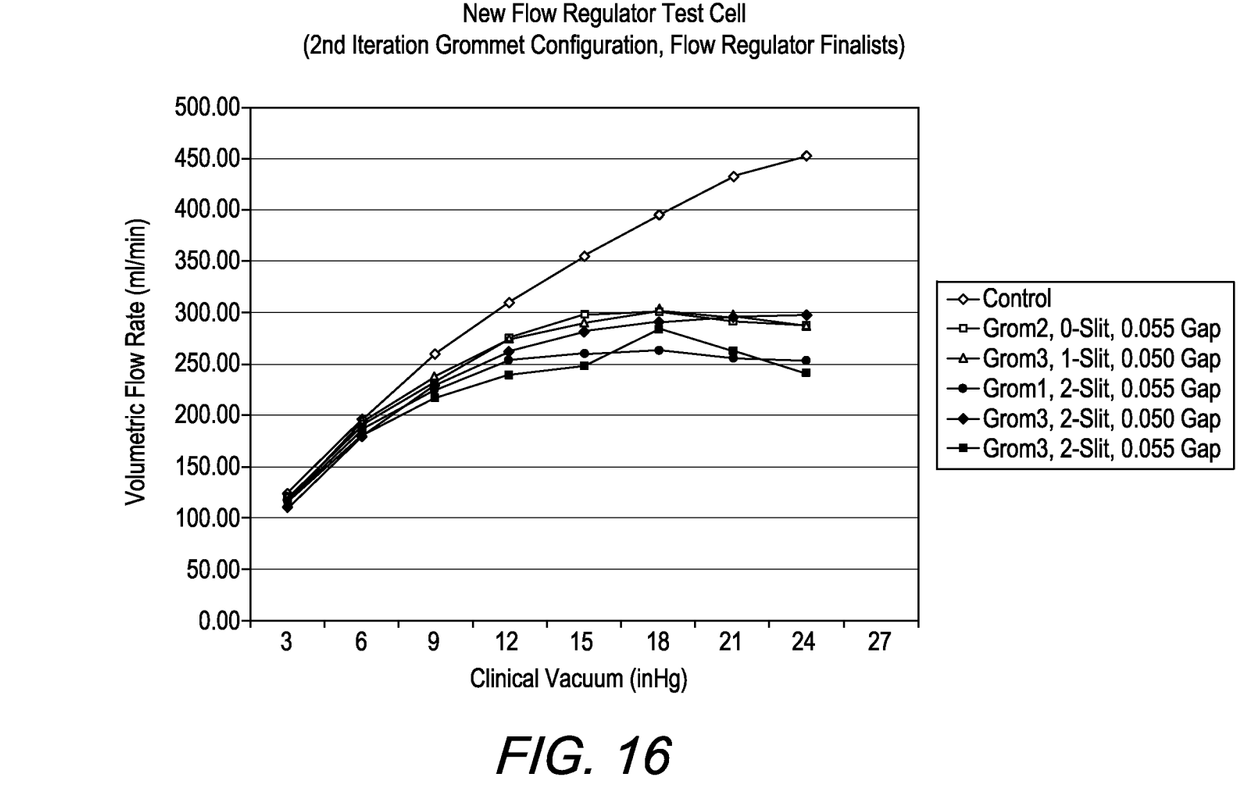

As shown in FIGS. 14-16, as clinical vacuum pressure (X axis, in inches of Mercury or InHg) increases, vacuum systems including embodiments of suction flow regulator 100, 200, 300 maintain a more regular volumetric flow rate (Y axis, in mL/min) than a control vacuum system without a suction flow regulator. Thus, embodiments of a suction flow regulator described herein provide automatic compensation so that vacuum requirements of the suction system are met while a more optimal suction effect is delivered at the distal end of a medical device.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting.

What is claimed as new and desired to be protected by Letters Patent of the United States is:

1. A suction flow regulator comprising:
an adapter having a distal and a proximal end and a vacuum flow path for allowing a vacuumed fluid to flow from said distal end to said proximal end; and
a device fixed inside said adapter, wherein said device is configured to permit air from outside said suction flow regulator to access a chamber within said vacuum flow path according to a vacuum level, wherein said device comprises a first grommet comprising a elastomeric material and having a distal end and a proximal end corresponding to said distal and proximal ends of said adapter, and a second grommet comprising a lower durometer elastomeric material than said first grommet, wherein said second grommet is configured to deflect during an increased vacuum level.

2. The suction flow regulator of claim 1, wherein said device is further configured to prevent air from outside said suction flow regulator from accessing said chamber when said vacuumed fluid is at a first vacuum level, and to permit air from outside said suction flow regulator to access said chamber when said vacuumed fluid is at a second vacuum level that is higher than said first vacuum level.

3. The suction flow regulator of claim 1, wherein said first grommet is rigid.

4. The suction flow regulator of claim 1, said first grommet further comprising:
   at least one slit integral to and traversing the first grommet; and
   at least one weep hole in said proximal end of said first grommet corresponding to said at least one slit.

5. The suction flow regulator of claim 4, wherein said second grommet is configured to deflect to expose said at least one slit at said distal end of said first grommet during said increased vacuum level.

6. The suction flow regulator of claim 4, wherein said at least one weep hole and said at least one slit comprises two weep holes and two slits.

7. The suction flow regulator of claim 4, wherein said at least one weep hole and said at least one slit comprises three weep holes and three slits.

8. The suction flow regulator of claim 7, wherein said three weep holes and three slits have dimensions of approximately 0.021 in; 0.026 in; and 0.031 in, respectively.

9. The suction flow regulator of claim 1, further comprising a vacuum system connected to said adapter, said adapter being configured to connect along a suction tube of said vacuum system.

10. The suction flow regulator of claim 9, wherein said vacuum system is an aspirating system for use with an ablation device.

11. The suction flow regulator of claim 10, wherein said aspirating system is integrated with said ablation device.

12. The suction flow regulator of claim 10, wherein said aspirating system is separate from said ablation device.

13. A device comprising:
   an ablation device including an ablation electrode at a distal end of said ablation device;
   an aspirating device for providing varying vacuum levels at said distal end of said ablation device, said aspirating device having a distal end and a proximal end and a suction tube for allowing a vacuumed fluid to flow from said distal end to said proximal end of said aspirating device; and
   a suction flow regulator connected along said suction tube, said suction flow regulator comprising:
   an adapter configured to connect along said suction tube, said adapter having a distal and a proximal end and a vacuum flow path for allowing said vacuumed fluid to flow from said distal end to said proximal end; and
   a device fixed inside said adapter, wherein said device is configured to permit air from outside said suction flow regulator to access a chamber within said vacuum flow path according to a vacuum level, wherein said aspirating device and said suction flow regulator are separate from said ablation device, and wherein said device comprises a first grommet comprising a elastomeric material and having a distal end and a proximal end corresponding to said distal and proximal ends of said adapter, and a second grommet comprising a lower durometer elastomeric material than said first grommet, wherein said second grommet is configured to deflect during an increased vacuum level.

14. The device of claim 13, wherein said suction flow regulator is connected at a proximal end of said suction tube.

* * * * *